United States Patent
Nakai et al.

(10) Patent No.: US 10,671,707 B2
(45) Date of Patent: Jun. 2, 2020

(54) ONLINE COACHING METHOD ENABLING ONLINE COMMUNICATION BETWEEN TRAINER AND TRAINEE

(71) Applicant: Panasonic Intellectual Property Management Co., Ltd., Osaka (JP)

(72) Inventors: Kentaro Nakai, Hyogo (JP); Toshihiro Sota, Osaka (JP); Yuka Ozawa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 153 days.

(21) Appl. No.: 15/049,147

(22) Filed: Feb. 22, 2016

(65) Prior Publication Data
US 2016/0250518 A1    Sep. 1, 2016

(30) Foreign Application Priority Data

Feb. 27, 2015 (JP) .................................. 2015-039434
Nov. 27, 2015 (JP) .................................. 2015-232196

(51) Int. Cl.
*G06F 19/00* (2018.01)
*G09B 19/00* (2006.01)

(52) U.S. Cl.
CPC ..... *G06F 19/3481* (2013.01); *G09B 19/0038* (2013.01)

(58) Field of Classification Search
CPC .................. G06F 19/3481; G09B 19/0038
See application file for complete search history.

(56) References Cited

U.S. PATENT DOCUMENTS

| | | | | |
|---|---|---|---|---|
| 2006/0205564 A1* | 9/2006 | Peterson | ............... | A63B 69/00 482/8 |
| 2008/0204225 A1* | 8/2008 | Kitchen | ............... | A63B 21/072 340/539.22 |
| 2010/0267521 A1* | 10/2010 | Matsunaga | ......... | G06F 19/3481 482/9 |
| 2011/0125680 A1* | 5/2011 | Bosworth | ........... | G06F 19/3431 706/12 |
| 2013/0014258 A1* | 1/2013 | Williams | ........... | G06Q 30/0241 726/24 |
| 2015/0141203 A1* | 5/2015 | Ohlsen | ............... | G06Q 10/0639 482/9 |
| 2016/0078191 A1* | 3/2016 | Casimiro | ............ | G06F 19/3418 705/3 |
| 2016/0243404 A1* | 8/2016 | Keller | ................ | G09B 19/0038 |
| 2016/0321948 A1* | 11/2016 | Adhikari | ............ | G09B 19/0038 |
| 2017/0274267 A1* | 9/2017 | Blahnik | ............. | A63B 24/0062 |

FOREIGN PATENT DOCUMENTS

JP        2004-016738        1/2004

\* cited by examiner

*Primary Examiner* — Dmitry Suhol
*Assistant Examiner* — Jason Skaarup
(74) *Attorney, Agent, or Firm* — Greenblum & Bernstein, P.L.C.

(57) ABSTRACT

An online coaching method includes: acquiring workout log data representing progress of workout carried out by a trainee who receives coaching for workout from a trainer; acquiring transmission status data representing a status of message transmission using a communication screen from the trainee to the trainer; and controlling permission and prohibition of message transmission from the trainee to the trainer on the communication screen based on the workout log data and the transmission status data.

15 Claims, 16 Drawing Sheets

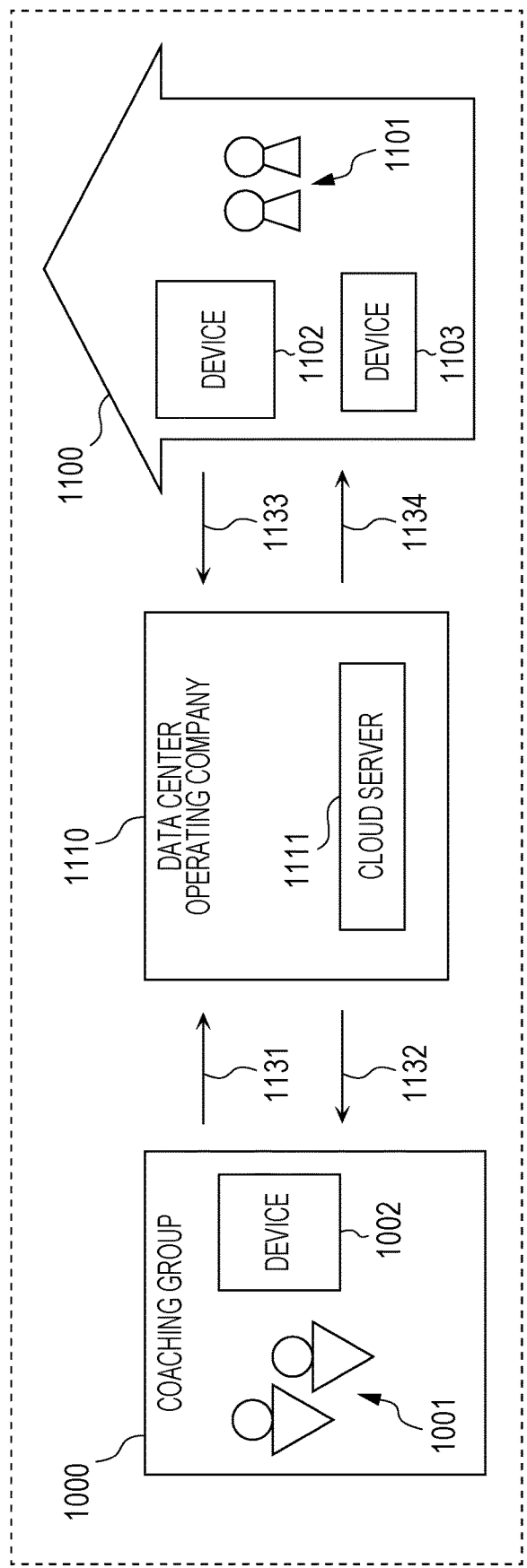
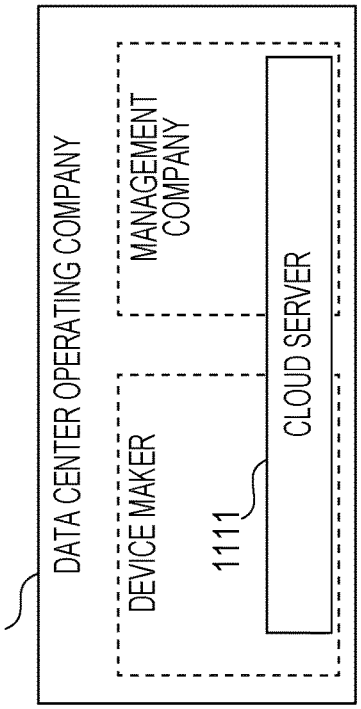
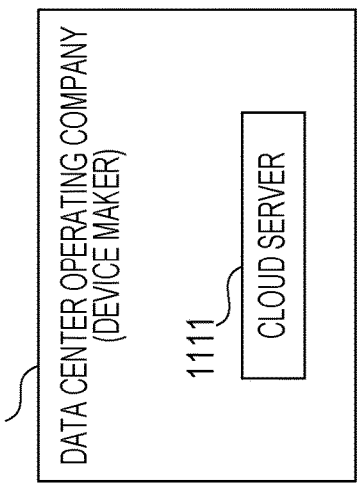

FIG. 4

| ID (401) | NAME (402) | TARGET n OF WORKOUTS/PERIOD (403) | LIMIT STATUS (404) | OPTION USE RIGHT (405) | DISPLAY TYPE (406) | THRESHOLD m OF TRANSMITTED MESSAGES/PERIOD (407) |
|---|---|---|---|---|---|---|
| 00001 | UNDO TARO | 10 WORKOUTS/WEEK | OFF | 1 | A | 8 MESSAGES/WEEK |
| 00002 | HIGASHI ICHIRO | 5 WORKOUTS/WEEK | OFF | 0 | B | 10 MESSAGES/WEEK |
| 00003 | NISHINO TERU | 3 WORKOUTS/WEEK | ON | 0 | C | 5 MESSAGES/WEEK |
| 00004 | MATSU TAKESHI | 10 WORKOUTS/WEEK | OFF | 0 | D | 10 MESSAGES/WEEK |

| ID | COMPLETED WORKOUTS | PERIOD | UPLOADS OF VITAL DATA |
|---|---|---|---|
| 00001 | 12 | 1 WEEK | 4 |
| 00002 | 11 | 1 WEEK | 5 |
| 00003 | 1 | 1 WEEK | 2 |
| 00004 | 2 | 1 WEEK | 1 |

FIG. 5B

| ID | TRANSMITTED MESSAGES | PERIOD |
|---|---|---|
| 00001 | 9 | 1 WEEK |
| 00002 | 3 | 1 WEEK |
| 00003 | 6 | 1 WEEK |
| 00004 | 1 | 1 WEEK |

FIG. 5C

| TRAINEE DISPLAY TYPE | FEEDBACK STRING |
|---|---|
| A | GREAT PACE, KEEP IT UP! |
| B | YOU ARE DOING AWESOME! DON'T BE SHY, SPEAK UP IF THERE'S ANYTHING YOU NEED TO KNOW. |
| C | JUST A BIT MORE WORK OUT, AND YOU CAN ASK THE TRAINER ANYTHING. LET'S TRY HARD TOGETHER! |
| D | LET'S START WITH WHAT YOU CAN DO. TELL ME WHAT YOU ARE UNSURE ABOUT. |
| Z | YOU TRIED REALLY HARD. YOU CAN ASK THE TRAINER ANYTHING NOW. |

ONLINE COACHING METHOD ENABLING ONLINE COMMUNICATION BETWEEN TRAINER AND TRAINEE

BACKGROUND

1. Technical Field

The present disclosure relates to an online coaching method and the like to control communication using a communication screen between a trainer and a trainee who receives coaching for workout from the trainer.

2. Description of the Related Art

Coaching systems represented by an online fitness menu presentation via the Internet have been developed (see Japanese Unexamined Patent Application Publication No. 2004-16738, for example).

SUMMARY

The aforementioned technique needs further improvements.

In one general aspect, the techniques disclosed here feature an online coaching method, the method including: acquiring workout log data representing progress of workout carried out by a trainee who receives coaching for workout from a trainer; acquiring transmission status data representing a status of message transmission using a communication screen from the trainee to the trainer; and controlling permission and prohibition of message transmission from the trainee to the trainer on the communication screen based on the workout log data and the transmission status data.

According to the aforementioned aspect, it is possible to achieve both the benefits of reducing burden on the trainer and keeping the trainee's motivation through appropriate advice and answers.

It should be noted that these general or specific embodiments may be implemented as a system, a device, an integrated circuit, a computer program, a storage medium such as CD-ROM which is computer-readable, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1A is a diagram illustrating an entire image of the service provided by an online coaching system in an embodiment;

FIG. 1B is a diagram illustrating an example of the embodiment where a device maker serves as a data center operating company;

FIG. 1C is a diagram illustrating an example of the embodiment where any one or both of a device maker and a management company serve as a data center operating company;

FIG. 4 is a table illustrating an example of membership information of the embodiment;

FIG. 5A is a diagram illustrating an example of workout log data of the embodiment;

FIG. 5B is a diagram illustrating an example of transmission status data of the embodiment;

FIG. 5C is a diagram illustrating an example of a display type table of the embodiment;

Figure 2:
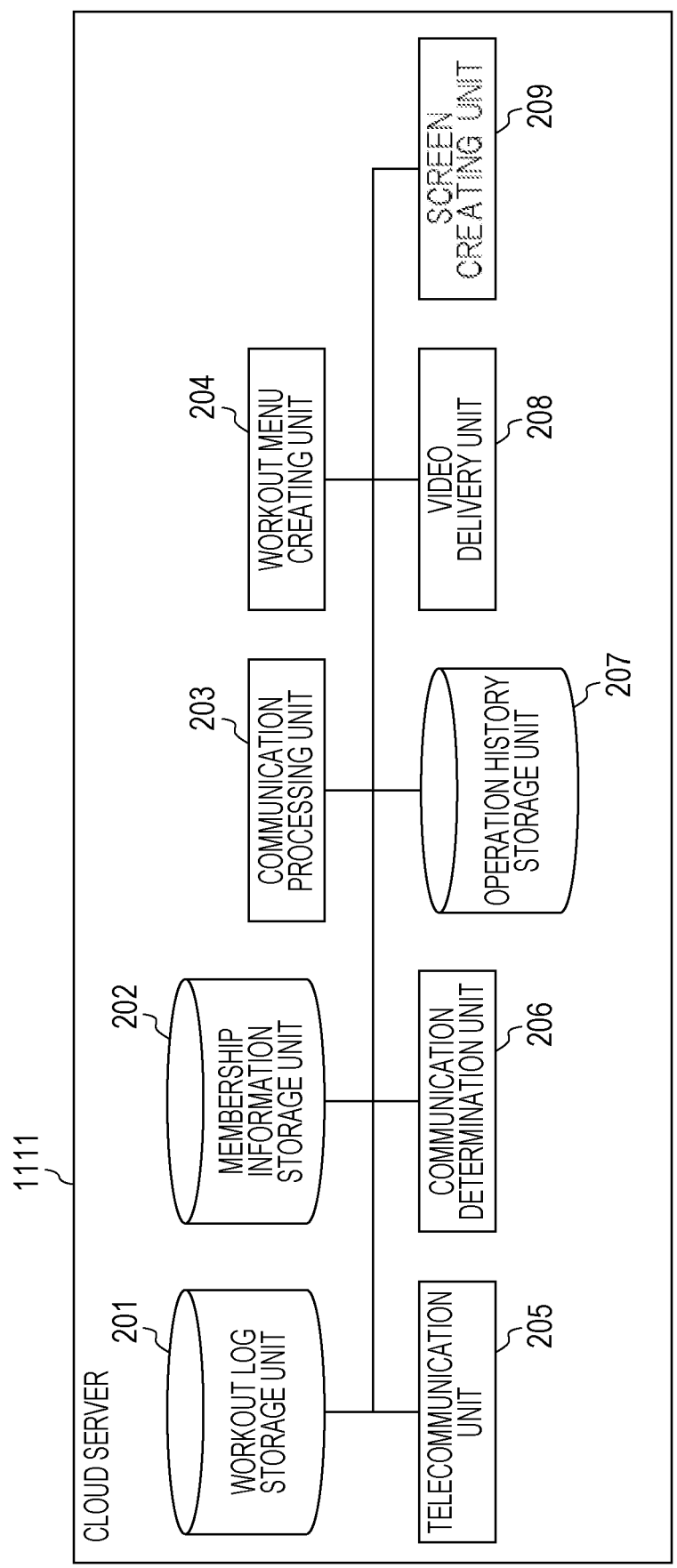
FIG. 2 is a block diagram illustrating the configuration of a cloud server in the embodiment.

DETAILED DESCRIPTION (Underlying Knowledge Forming Basis of the Present Disclosure)

Online coaching between a trainer and trainees sometimes places heavy burden on the trainer because the trainer gives advices to a number of trainees or answers questions from the trainees.

If the system entirely gives advice and answers to trainees automatically in order to reduce the burden on the trainer, advices and answers are presented with predetermined phrases, causing the trainees to get bored. This results in lowering trainees' motivation to work out.

On the other hand, it takes too much time for the trainer to manually give advices and answers to every trainee, and this places heavy burden on the trainer.

As disclosed in Japanese Unexamined Patent Application Publication No. 2004-16738, techniques to full-automatically send advices and messages to trainees have been studied. However, trainees feel uncomfortable seeing mechanical messages. On the other hand, trainers, who provide services, need to provide better services for as many trainees as possible and keep trainees' motivation with fewer man-hours. The technical solutions to satisfy the aforementioned needs have not been studied.

Based on the above-described considerations, the inventors have achieved each aspect of the present disclosure.

In one general aspect, the techniques disclosed here feature an online coaching method, the method including: acquiring workout log data representing progress of workout by a trainee who receives coaching for workout from a trainer; acquiring transmission status data representing a status of message transmission using a communication screen from the trainee to the trainer; and controlling permission and prohibition of the message transmission from the trainee to the trainer on the communication screen based on the workout log data and the transmission status data.

According to the aspect, the online coaching method controls permission and prohibition of the message transmission from the trainee to the trainer through the communication screen based on the workout log data and transmission status data. Accordingly, it is possible to prohibit transmission of unnecessary messages from the trainee to the trainer. Moreover, by replying to a message received from the trainee who is permitted to transmit messages, the trainer can send advice and answers appropriate for the trainee and can keep up the trainee's motivation.

The workout log data represents the number of workouts completed by the trainee, and the message transmission from the trainee to the trainer may be permitted when the number of workouts completed by the trainee is larger than a predetermined target number of workouts.

According to the aspect, the message transmission is permitted when the number of workouts completed by the trainee is larger than the predetermined target number of workouts. Accordingly, the online coaching method allows the trainer to increase the trainee's motivation to work out while reducing the burden on the trainer due to online communication with trainees.

The transmission status data may represent the number of messages transmitted from the trainee to the trainer for a predetermined period of time, and the message transmission from the trainee to the trainer may be prohibited when the number of workouts completed by the trainee is not larger than the predetermined target number of workouts and the number of messages transmitted from the trainee to the trainer is larger than a predetermined threshold of transmitted messages.

According to the aspect, permission and prohibition of the message transmission can be controlled based on the number of workouts completed and the number of messages transmitted. Accordingly, the online coaching method can suppress an increase in the number of messages transmitted, thus reducing the burden on the trainer.

The online coaching method may further include: determining a phrase to be displayed on the communication screen based on the result of comparison between the number of completed workouts and the target number of workouts and the result of comparison between the number of messages transmitted and the threshold of transmitted messages.

According to the aspect, the phrase to be displayed on the communication screen is determined based on the number of workouts completed and the number of messages transmitted. Accordingly, the trainer and the trainee check the phrase displayed on the communication screens to know the workout log and the message transmission status and keep up motivation for the workouts and the message transmission.

The workout log data may represent the number of uploads of measured vital data to a server from the trainee, and the message transmission from the trainee to the trainer may be permitted when the number of uploads of the vital data is larger than a predetermined target number of uploads.

According to the aspect, permission and prohibition of the message transmission can be controlled based on the number of uploads of vital data.

Accordingly, it is possible to promote uploading of vital data.

It should be noted that these general or specific embodiments may be implemented as a system, a device, an integrated circuit, a computer program, a storage medium such as CD-ROM which is computer-readable, or any selective combination thereof.

(Entire Image of Provided Service)

First, a description is given of the entire image of services provided by an online coaching system in the present disclosure.

FIG. 1A is a diagram illustrating the entire image of a service provided by the online coaching system in the present disclosure. The online coaching system includes one or more coaching groups 1000, a data center operating company 1110, and one or more trainee groups 1100.

The coaching group 1000 can be of any scale and, for example, is a corporation such as a fitness club, an association, or a private business. The coaching group 1000 includes one or plural trainers 1001. The trainers 1001 are an example of trainers and use one or plural devices 1002. The one or plural devices 1002 are an example of a first device and includes a device connectable to the Internet (a smart phone, a personal computer (PC), a television, or the like, for example). The one or plural devices 1002 may include a device which is not connectable to the Internet directly but is connectable to the Internet via a home gateway (not illustrated).

The trainee group 1100 can be of any scale and, for example, is a corporation, an association, or a household. The trainee group 1100 includes one or plural trainees 1101.

The trainees 1101 are people who receive coaching for workout from the trainers 1001 and use one or plural devices 1102 and devices 1103. The one or plural devices 1102 are an example of a second device and includes a device connectable to the Internet (a smart phone, a personal computer (PC), a television, or the like, for example).

The devices 1103 include a device capable of measuring vital data of the trainee 1101 (a body composition scale, an activity tracker, a sphygmomanometer, or a heart rate meter, for example). The devices 1103 may include a device which is not connectable to the Internet directly itself but is connectable to the Internet via the one or plural devices 1102 or a home gateway (not illustrated).

The data center operating company 1110 includes a cloud server 1111. The cloud server 1111 is a virtual server which cooperates with various devices via the Internet. The cloud server 1111 mainly manages big data, for example, which is too large to handle with normal database management tools or the like. The data center operating company 1110 performs management of data, management of the cloud server 1111, operation of the data center which performs such management, and the like. The details of the services performed by the data center operating company 1110 are described later.

It should be noted that the server managed by the data center operating company 1110 is not limited to the virtual server and may be a computer physically provided with an external storage device such as a CPU, a memory, or a hard disk drive (HDD). The server may be composed of a personal computer.

Herein, the data center operating company 1110 is not limited to a company which performs only management of data or only management of the cloud server 1111. For example, as illustrated in FIG. 1B, when a device maker that develops or manufactures one of the plural devices 1002 performs management of data, management of the cloud server 1111, or the like, the device maker serves as the data center operating company 1110. The data center operating company 1110 is not limited to one company. For example, as illustrated in FIG. 1C, when a device maker and a management company perform management of data or management of the cloud server 1111 in cooperation or by sharing the same, any one or both of the device maker and the management company serve as the data center operating company 1110.

Next, a description is given of a flow of information in the online coaching system illustrated in FIG. 1A.

The trainer 1001 acquires data from the cloud server 1111 of the data center operating company 1110 by using the device 1002 and displays an application screen on the device 1002 (arrows 1131 and 1132).

On the device 1002, the trainer 1001 creates a workout menu appropriate for the trainee 1101 and performs an operation for communication with the trainee 1101. The data inputted on the device 1002 by the trainer 1001 is managed on the cloud server 1111 (arrow 1131).

The trainee 1101 acquires data from the cloud server 1111 of the data center operating company 1110 by using the device 1102 and displays an application screen on the device 1102 (arrows 1133 and 1134).

On the device 1102, the trainee 1101 displays the workout menu inputted by the trainer 1001 and views a video of the presented workout menu. The video is delivered from the cloud server 1111 (the arrow 1134).

When the trainee 1101 views the video, viewing history data is transmitted to the cloud server 1111 (the arrow 1133).

The histories of accesses to the cloud server 1111 and operations performed on the application by the trainee 1101 so as to use the online coaching service are stored in the cloud server 1111 (arrow 1133).

The trainee 1101 checks an advice transmitted from the trainer 1001 on the communication screen displayed on the device 1102.

The trainee 1101 inputs a question to the trainer 1001 on the device 1102 if necessary. The data inputted at the device 1102 is managed in the cloud server 1111.

The trainee 1101 uses the device 1103 to measure vital data of the trainee 1101 and transmits the data to the cloud server 1111 (arrow 1133).

Hereinafter, the embodiment is specifically described with reference to the drawings.

Note that the embodiment described below shows general or specific examples. The numerical values, shapes, constituent elements, the positions of the constituent elements, and the connecting style thereof, steps, the order of the steps are shown by way of example and do not limit the claims. Additionally, some of the constituent elements of the embodiment below that are not described in independent claims showing the broadest idea are described as optional constituent elements. Moreover, the contents of each embodiment can be appropriately combined.

Embodiment

The embodiment shows an example in which the coaching group is a fitness club and the trainee group is a general household which receives an online coaching service. Each trainer belonging to the coaching group takes charge of providing services to plural trainees previously determined.

[Configuration of Cloud Server]

The configuration of the cloud server 1111 is described with reference to FIG. 2. FIG. 2 is a block diagram illustrating the configuration of the cloud server of the embodiment.

The cloud server 1111 includes a telecommunication unit 205, a communication processing unit 203, a communication determination unit 206, a workout menu creating unit 204, a video delivery unit 208, a screen creating unit 209, a workout log storage unit 201, a membership information storage unit 202, and an operation history storage unit 207.

The telecommunication unit 205 is connected to a network and is configured to communicate with the device 1002 of the coaching group 1000 and the device 1102 of the trainee group 1100 via the network.

The telecommunication unit 205 is a communication interface for a wired or wireless local area network (LAN), for example.

The screen creating unit 209 refers to membership information stored in the membership information storage unit 202 to create trainer's screen data and trainee's screen data.

In the embodiment, the screen creating unit 209 outputs the trainer's screen data to the trainer's device 1002 through the telecommunication unit 205 in response to an access to a webpage for trainers in the cloud server 1111 from the trainer's device 1002, for example. Moreover, the screen creating unit 209 outputs the trainee's screen data to the trainee's device 1102 through the telecommunication unit 205 in response to an access to a webpage for trainees in the cloud server 1111 from the trainee's device 1102.

The workout menu creating unit 204 creates a workout menu appropriate for each trainee who receives coaching from the trainer based on an operation instruction from the trainer. The created workout menu is stored in the membership information storage unit 202 in association with the corresponding trainee. The stored workout menu is provided to the trainee when the trainee accesses the webpage of the cloud server 1111.

In the embodiment, the workout menu is a list of exercises including stretches, yoga, muscle training, cooling down, and the like, for example.

The video delivery unit 208 delivers video contents of workouts to the trainee's device 1102 through the telecommunication unit 205 in accordance with a reproduction instruction from the trainee's device 1102.

In the embodiment, the delivered video contents are those of stretches, yoga, muscle training, cooling down, and the like included in the workout menu which the trainee has received, for example.

Note that the video contents are stored in a storage device (not illustrated).

The communication processing unit 203 receives from the trainer's device 1002 through the telecommunication unit 205 an advice or answer message from the trainer to the trainee. The communication processing unit 203 then reflects the received advice or answer message on the trainee's communication screen and trainer's communication screen through the screen creating unit 209.

Moreover, the communication processing unit 203 receives from the trainee's device 1102 through the telecommunication unit 205 a question message of the trainee to the trainer. The communication processing unit 203 then reflects the received question message on the trainee's communication screen and trainer's communication screen.

Figure 6:
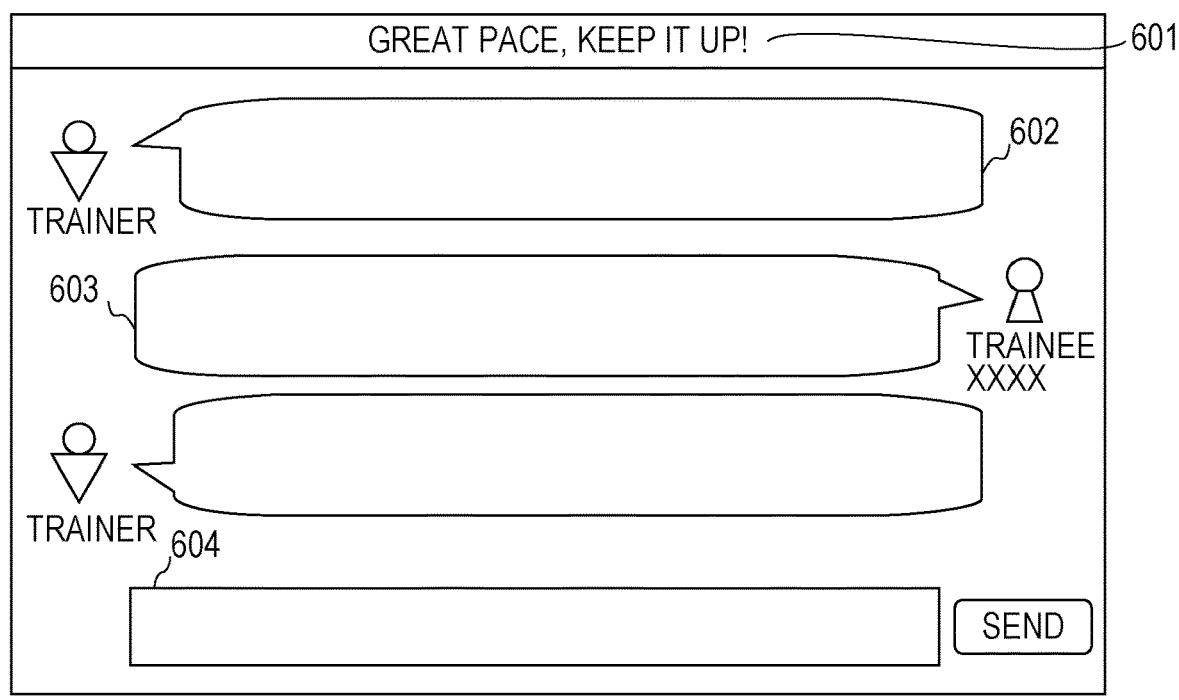
FIG. 6 is a diagram illustrating an example of communication screens of the embodiment.

Herein, the communication screens are specifically described with reference to FIG. 6. FIG. 6 illustrates an example of the communication screens in the embodiment.

A communication screen 600 illustrated in FIG. 6 includes a field 601 indicating the workout log and the transmission status, a trainer's message content 602, a trainee's message content 603, and an input field 604 to input a message.

In the embodiment, the layout of the trainer's communication screen is the same as the layout of the trainee's communication screen.

The trainee refers to the field 601 indicating the workout log and the transmission status to know the summary of the workout log of the trainee and the transmission status of messages from the trainee to the trainer using the communication screen.

Further, the trainer also refers to the field 601 to know the summary of the workout log of the trainee and the transmission status of messages from the trainee to the trainer using the communication screen.

Advice messages and answer messages from the trainer to the trainee's questions are indicated as the trainer's message content 602.

Messages from the trainee to the trainer are indicated as the trainee's message content 603.

A message inputted in the input field 604 by the trainer or the trainee is transmitted to the cloud server 1111 when a send button is pressed by the trainer or the trainee.

Note that a message that the trainee replies to advice from the trainer to the trainee is managed by the cloud server 1111.

The trainer and the trainee refer to the same screen illustrated in FIG. 6 by using the devices 1002 and 1102, respectively.

The layout of the communication screen illustrated in FIG. 6 is shown by way of example, and the present disclosure is not limited thereto. For example, the locations of icons representing the trainer and the trainee, the fields representing the workout log and the transmission status, and the input field are not limited to the positions illustrated in FIG. 6. For example, the icons for the trainee may be located on the left side while the icons for the trainer are located on the right side.

The trainer's communication screen and the trainee's communication screen may have designs (colors, fonts, images, and arrangement, for example) different from each other.

The communication determination unit 206 determines whether to permit the trainee, who receives coaching from the trainer, to send a message to the trainer based on the workout log of the trainee and the status of message transmission from the trainee to the trainer. The detailed configuration is described later.

The membership information storage unit 202 is an HDD or a semiconductor memory, for example. The membership information storage unit 202 stores membership information of the trainees (members) using the online coaching service.

Herein, the membership information is specifically described with reference to FIG. 4. FIG. 4 illustrates an example of the membership information in the embodiment.

Membership information 400 includes an ID field 401, a name field 402, a target number n of workouts/period field 403, a limit status field 404, an option use right field 405, a display type field 406, and a threshold m of transmitted messages/period field 407.

When a trainee starts using the online coaching service, an identifier and name of the trainee are registered in the ID field 401 and the name field 402, respectively.

In the target number n of workouts/period field 403, the target number of workouts per unit period of each trainee who receives coaching from the trainer is registered. Specifically, in FIG. 4, the target number of workouts registered for the trainee with an identifier of "00001" and a name of "Undo Taro" is "10 workouts per week".

In the limit status field 404, information on whether the message transmission from the trainee to the trainer is limited is registered based on the result of processing by the communication determination unit 206.

In the option use right field 405, information on whether the trainee is allowed to use an optional service as a reward for achieving the workout target or the like is registered based on the result of processing by the communication determination unit 206.

In the display type field 406, information for determining the content to be displayed on the communication screen is registered based on the result of processing by the communication determination unit 206.

In the threshold m of transmitted messages/period field 407, the threshold (the upper limit) of the number of messages allowed to be transmitted per unit period from each trainee to the trainer is registered. The threshold m of transmitted messages/period field 407 is registered for each trainee by the trainer. Further, the threshold m of transmitted messages/period field 407 is updated by the communication determination unit 206 based on the workout log and the message transmission status of the trainee.

It should be noted that the membership information may include vital data of each trainee uploaded to the cloud server 1111. Specifically, the membership information may include vital data of each trainee measured by a device, such as an activity tracker or a body composition meter, in association with the ID of the trainee.

The trainer and the trainees who receives coaching from the trainer are associated with each other and to be recorded in the membership information storage unit 202.

Note that the membership information also includes the address and contact information (such as telephone number or mail address, for example) of each trainee, which are necessary for the actual operation of the online coaching service (not illustrated in FIG. 4).

The membership information storage unit 202 in the embodiment may store the membership information in any kind of format. The membership information storage unit 202 may be implemented by a relational database or a NoSQL, for example.

The workout log storage unit 201 is composed of an HDD or a semiconductor memory, for example. The workout log storage unit 201 stores the workout log data of the trainee using the online coaching system. In this embodiment, the workout log data represents the progress of workout by the trainee. Specifically, the workout log data represents the number of workouts that have been completed by the trainee, for example. Moreover, the workout log data may represent the number of times that the trainee's vital data is uploaded to the cloud server 1111, for example.

Herein, the workout log data is specifically described with reference to FIG. 5A. FIG. 5A illustrates an example of the workout log data in the embodiment.

Workout log data 500 includes an ID field 501, a number of completed workouts field 502, a period field 503, and a number of uploads of vital data field 504.

In the ID field 501, the ID of the trainee is registered. In the number of completed workouts field 502, the number of workouts that the trainee has completed is registered. The number of completed workouts is obtained by counting the number of times that the trainee views video contents in accordance with the workout menu transmitted from the trainer, for example. In FIG. 5A, the number of completed workouts of the trainee with an ID of "00001" is "12".

The value of the number of completed workouts field 502 is, for example, reset to 0 every period determined by the period field 503 (every week, for example). The value of the number of completed workouts field 502 may be updated with a period shorter than the period determined by the period field 503. In this case, the value of the number of completed workouts field 502 is updated with reference to the operation history data for corresponding period, for example.

The number of completed workouts is not limited to the value obtained by counting the number of viewing of video contents. For example, the cloud server 1111 may accept an input of results of workouts performed outside of home or at facilities of the fitness club from the trainee through the device 1102.

In the period field 503, the period for counting the number of completed workouts is registered. For example, the period to achieve the target number of workouts that the trainer sets when creating the workout menu is registered in the period field 503 by the trainer. In FIG. 5A, the trainee with an ID of "00001" conducts the workout menu "12 times" in "one week" from the start of workout.

In the number of uploads of vital data field 504, the number of times the trainee uploads the vital data to the cloud server 1111 for the period registered in the period field 503 is registered.

Note that the vital data may be uploaded by direct transmission to the cloud server 1111 from the device 1103 that has measured the vital data or by manual input by the trainee.

The workout log storage unit 201 of the embodiment may store the workout log data in any kind of format. The workout log storage unit 201 may be implemented by a relational database or a NoSQL, for example.

The operation history storage unit 207 is an HDD or a semiconductor memory, for example. The operation history storage unit 207 stores data concerning the transmission status of messages from each trainee to the trainer and the history data of operations performed for the online coaching system by the trainee.

Herein, the transmission status data is specifically described with reference to FIG. 5B. FIG. 5B illustrates an example of the transmission status data in the embodiment.

Transmission status data 505 includes an ID field 506, a number of transmitted messages field 507, and a period field 508.

In the ID field 506, the identifier of each trainee is registered.

In the number of transmitted messages field 507, it is registered how many times the trainee has transmitted messages to the trainer using the communication screen. Specifically, the value of the number of transmitted messages field 507 represents the number of messages that the trainee has inputted for the trainer on the communication screen.

For example, the value of the number of transmitted messages field 507 is reset to 0 every period determined by the period field 508 (every week, for example). The value of the number of transmitted messages field 507 may be updated with a shorter period than the period determined by the period field 508. In this case, the value of the number of transmitted messages field 507 is updated with reference to the operation history data for the corresponding period, for example.

In the period field 508, the period for counting the number of transmitted messages is registered. The period is determined by the trainer when creating the workout menu for each trainee. In FIG. 5B, the trainee with an ID of "00001" sent "nine messages" in "one week".

Note that the operation history data includes how many times the trainee has accessed the cloud server 1111 to use the service, the dates and times of the trainee's accesses, how many times the trainee has logged in the cloud server 1111 per period, and the like (not illustrated).

The operation history storage unit 207 of the embodiment may store the transmission status data and the operation history data in any kind of format. For example, the operation history storage unit 207 may be implemented by a relational database or NoSQL, for example.

Based on the membership information stored in the membership information storage unit 202 and the transmission status data stored in the operation history storage unit 207, the trainer knows information of each trainee that the trainer is coaching.

Figure 8:
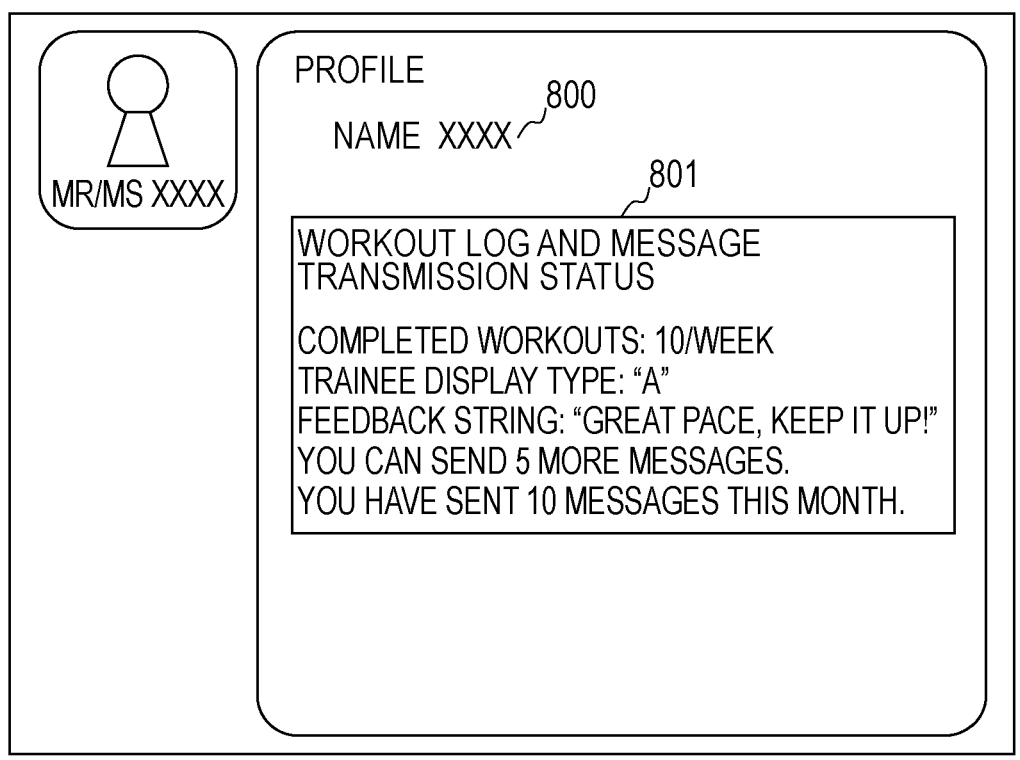
FIG. 8 is a diagram illustrating an example of a membership information screen of the embodiment.

FIG. 8 illustrates an example of the membership information screen for the trainer to check the information of the trainee in the embodiment.

As illustrated in FIG. 8, the membership information screen includes a field 800 indicating the name of the trainee and a field 801 indicating the workout log and the transmission status of the trainee.

Figure 3:
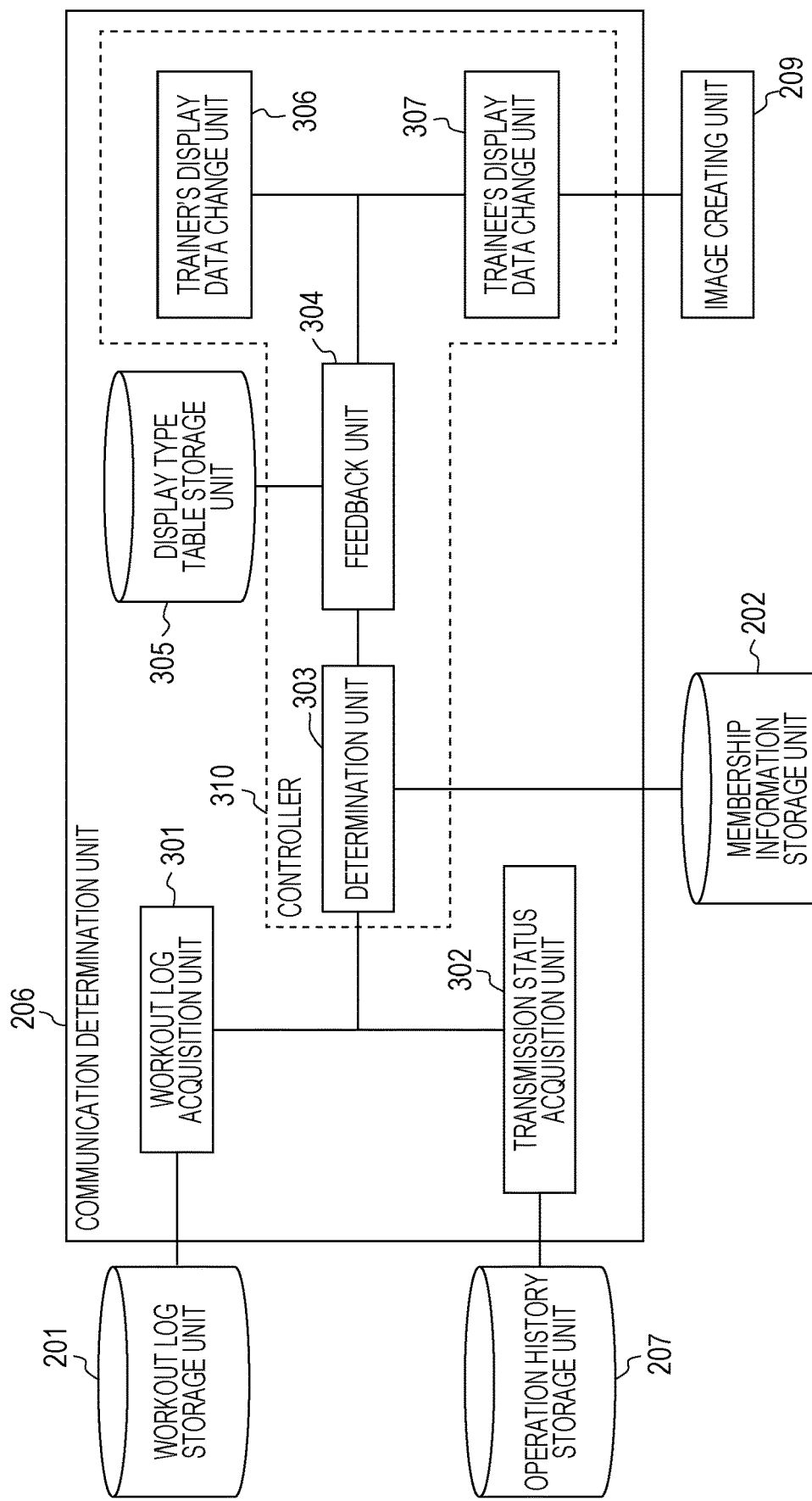
FIG. 3 is a block diagram illustrating an example of the configuration of a communication determination unit of the embodiment.

Next, the detailed configuration of the communication determination unit 206 is described with reference to FIG. 3. FIG. 3 is a block diagram illustrating an example of the configuration of the communication determination unit 206 of the embodiment.

The communication determination unit 206 includes a workout log acquisition unit 301, a transmission status acquisition unit 302, a display type table storage unit 305, and a controller 310.

The workout log acquisition unit 301 acquires workout log data of a trainee who receives coaching from the trainer from the workout log storage unit 201 and outputs the same to the controller 310.

The transmission status acquisition unit 302 acquires the transmission status data of the trainee from the operation history storage unit 207 and outputs the same to the controller 310.

The controller 310 permits or prohibits the message transmission from the trainee to the trainer on the communication screen based on the workout log data and the transmission status data. As illustrated in FIG. 3, the controller 310 includes a determination unit 303, a feedback unit 304, a trainer's display data change unit 306, and a trainee's display data change unit 307.

The determination unit 303 determines based on the workout log data and the transmission status data whether to permit the trainee to transmit a message. Based on the result of determination, the determination unit 303 determines the trainee display type that is used to determine a phrase to be displayed on the communication screen or the like.

The result of determination is recorded in the membership information storage unit 202 as the membership information. Specifically, based on the result of determination, the determination unit 303 updates the values of the limit status field 404, the option use right field 405, and the display type field 406 of the record specified by the ID of the trainee.

The feedback unit 304 acquires a feedback string corresponding to the trainee display type determined by the determination unit 303, from the display type table recorded in the display type table storage unit 305. The feedback unit 304 transmits the feedback string acquired from the display type table to the trainer's display data change unit 306 and trainee's display data change unit 307 together with the ID of the trainee.

Herein, the display type table is specifically described with reference to FIG. 5C. FIG. 5C illustrates an example of the display type table in the embodiment.

The display type table 509 includes a trainee display type field 510 and a feedback string field 511.

In the trainee display type field 510, the trainee display type is registered, which is an identifier representing the result of determination performed by the determination unit 303 based on the workout log data and the transmission status data.

In the feedback string field 511, a phrase which corresponds to the trainee display type and is to be displayed on the communication screen is registered.

In FIG. 5C, "Great pace, keep it up!" is registered as the feedback string corresponding to a trainee display type of "A".

Note that the "feedback strings" in the display type table 509 can be changed by the trainer or a system administrator.

The system may use the same display type table 509 or may use different display type tables 509 for different trainees. In the case of using different display type tables 509 for different trainees, the display type tables 509 are associated with the respective trainee's IDs for management.

The trainer's display data change unit 306 outputs the feedback string received from the feedback unit 304 to the communication screen and membership information screen through the screen creating unit 209.

The trainee's display data change unit 307 outputs the feedback string received from the feedback unit 304 to the communication screen through the screen creating unit 209.

[Operation of Online Coaching System]

Hereinafter, a description is given of the operation of the online coaching system configured as described above.

Figure 9:
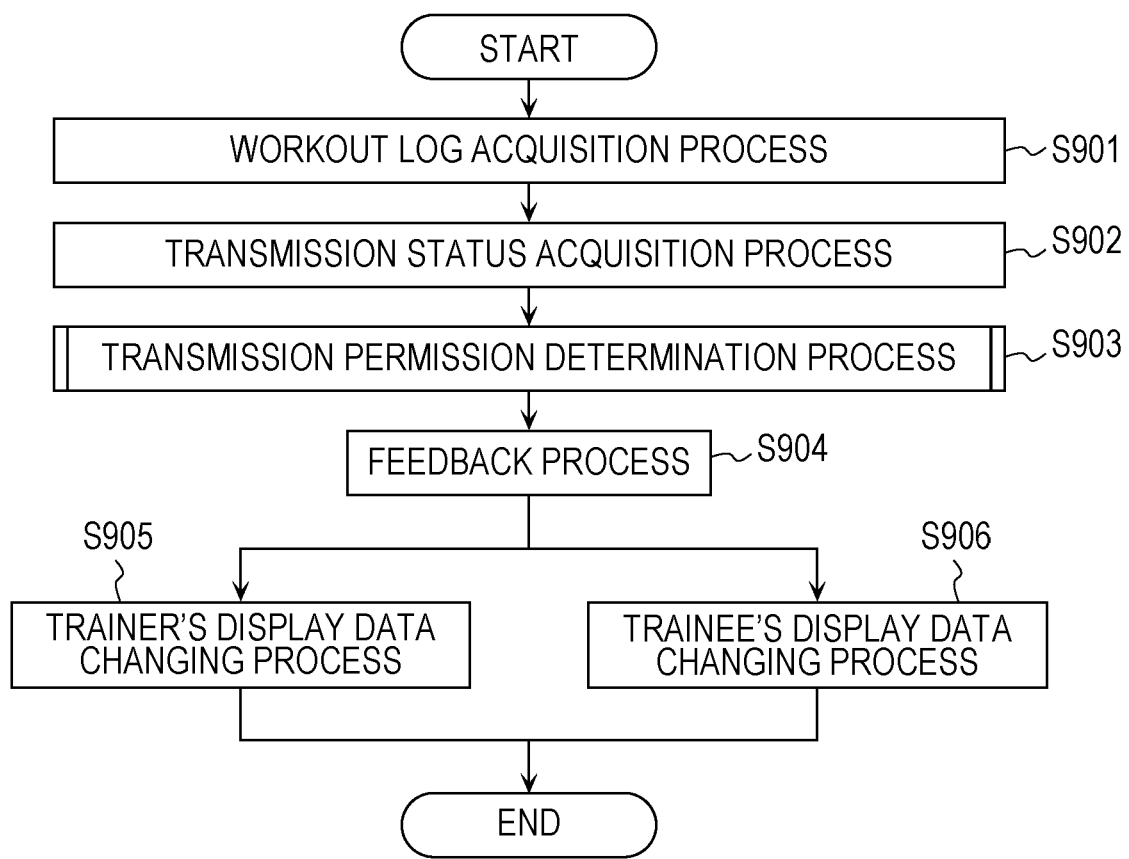
FIG. 9 is a flowchart illustrating processing of the communication determination unit of the embodiment.

FIG. 9 is a flowchart illustrating processing of the online coaching system in the embodiment.

In this embodiment, the determination whether to permit the message transmission is performed when the trainee sends a message to the trainer and when the trainee updates the own workout log data.

The online coaching system may be configured to automatically perform the process to determine whether to permit the message transmission at a certain time once a day. At this time, the process to determine whether to permit the message transmission is performed for all the trainees who are using the online coaching system.

First, the workout log acquisition unit 301 acquires from the workout log storage unit 201, the workout log data concerning a trainee who has updated the workout log (S901).

Next, the message transmission status acquisition unit 302 acquires the transmission status data concerning the trainee from the operation history storage unit 207 (S902).

Based on the acquired workout log data and transmission status data, the determination unit 303 determines whether to permit the message transmission from the trainee to the trainer on the communication screen and determines the trainee display type corresponding to the result of determination (S903).

Specifically, the determination unit 303 determines to permit the message transmission from the trainee to the trainer when the number of workouts completed by the trainee is larger than the predetermined target number of workouts. The determination unit 303 determines to prohibit the message transmission from the trainee to the trainer when the number of workouts completed by the trainee is smaller than the predetermined target number of workouts and the number of messages transmitted from the trainee to the trainer is larger than the predetermined threshold of transmitted messages. The processing of the step S903 is described later in more detail using FIG. 10.

The feedback unit 304 refers to the display type table 509 to select a feedback string corresponding to the trainee display type determined by the determination unit 303 and transmits the selected feedback string to the trainer's display data change unit 306 and trainee's display data change unit 307 (S904). Specifically, the feedback unit 304 determines a phrase (the feedback string in this case) to be displayed on the communication screens using the trainee display type based on the result of comparison between the number of workouts completed and the target number of workouts and the result of comparison between the number of messages transmitted and the threshold of transmitted messages.

The trainer's display data change unit 306 applies the feedback string received from the feedback unit 304 to the membership information screen and the communication screen (S905).

The trainee's display data change unit 307 applies the feedback string received from the feedback unit 304 to the communication screen (S906).

Next, the process to determine whether to permit the message transmission (S903) in FIG. 9 is described in detail with reference to FIG. 10.

Figure 10:
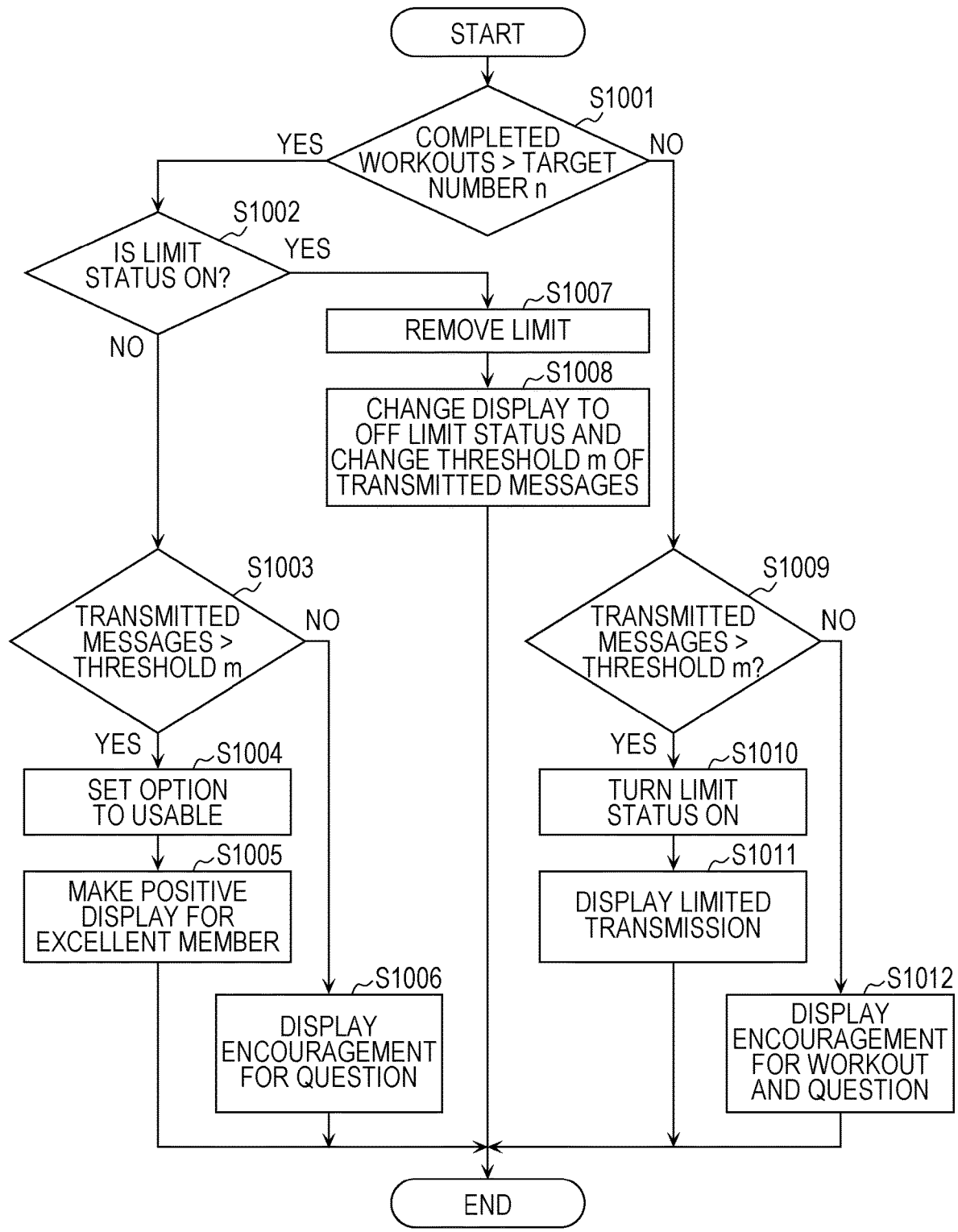
FIG. 10 is a flowchart illustrating details of a transmission permission determination process by the communication determination unit of the embodiment.

FIG. 10 illustrates a flowchart of the process to determine whether to permit the message transmission in the embodiment.

The determination unit 303 compares the number of workouts completed by the trainee, which is included in workout log data 500 and acquired by the workout log acquisition unit 301, with the target number of workouts of the trainee, which is included in membership information 400 (S1001). For example, when the ID of the trainee is "00001", the determination unit 303 compares "10 workouts/week" as the target number of workouts included in the membership information 400 illustrated in FIG. 4 with "12" as the number of completed workouts included in the workout log data 500 illustrated in FIG. 5A.

At this moment, if the number of completed workouts is larger than the target number of workouts (YES in S1001), the determination unit 303 refers to the membership information 400 to check whether the limit status of transmission on the trainee is ON (S1002).

When the limit status of transmission is ON (YES in S1002), the determination unit 303 once removes the limit of transmission on the trainee (S1007). In other words, the determination unit 303 permits the message transmission from the trainee to the trainer when the number of workouts completed by the trainee is larger than the predetermined target number of workouts.

In this process, the determination unit 303 updates the limit status field 404 and the display type field 406 in the membership information 400 (S1008). Specifically, the determination unit 303 updates the limit status field 404 included in the membership information 400 of the trainee to "OFF" and updates the display type field 406 of the trainee to "Z". The determination unit 303 initializes the value of the threshold m of transmitted messages/period field 407 included in the membership information 400 of the trainee.

The feedback unit 304 refers to the display type table 509 to acquire a feedback string corresponding to the determined display type. The feedback unit 304 transmits the acquired feedback string to the trainer's and trainee's display data change units 306 and 307. The trainer's and trainee's display data change units 306 and 307 change the workout log data and the transmission status data to be displayed on the communication screens and the membership information screen.

Specifically, when the limit of transmission is removed, the feedback unit 304 refers to the display type table 509 illustrated in FIG. 5C to acquire a feedback string of "You tried really hard. You can ask the trainer anything now." corresponding to the trainee display type of "Z".

When the limit status of transmission is OFF (NO in S1002), the determination unit 303 determines whether the number of messages transmitted from the trainee to the trainer is larger than the threshold of transmitted messages set for the trainee (S1003).

When the number of messages transmitted from the trainee to the trainer is larger than the threshold of transmitted messages (YES in S1003), the determination unit 303 updates the value of the option use right field in the membership information 400 to "1" so that the trainee can use an optional service (S1004).

The trainee who has acquired the right to use the optional service is allowed to input a new emoji (pictorial symbol) on the communication screen or is allowed to transmit a message to a famous trainer different from the current trainer who is coaching the trainee, for example. Note that the optional service does not need to be limited to a particular service.

The trainee's right to use an optional service may be terminated once the trainee uses the optional service or may be terminated in accordance with the workout log and the message transmission status.

The determination unit 303 determines that the trainee display type of the trainee is positive display type for an excellent member and registers the result of determination in the membership information (S1005).

Specifically, the determination unit 303 determines that the trainee display type is "A" and registers the determined trainee display type in the display type field 406 of the membership information 400.

In this process, the feedback unit 304 transmits to the trainer's and trainee's display data change units 306 and 307, a feedback string of "Great pace, keep it up!" corresponding to the determined trainee display type A. As illustrated in FIGS. 6 and 8, the string of "Great pace, keep it up!" is therefore displayed on the communication screens and the membership information screen (S1005).

On the other hand, when the number of transmitted messages is equal to or not larger than the threshold of transmitted messages (NO in S1003), the determination unit 303 sets the trainee display type to a display type which indicates that the trainer wants the trainee to transmit more messages. Specifically, the determination unit 303 sets the trainee display type to "B" and registers the determined trainee display type in the display type field 406 of the membership information 400.

Figure 11A:
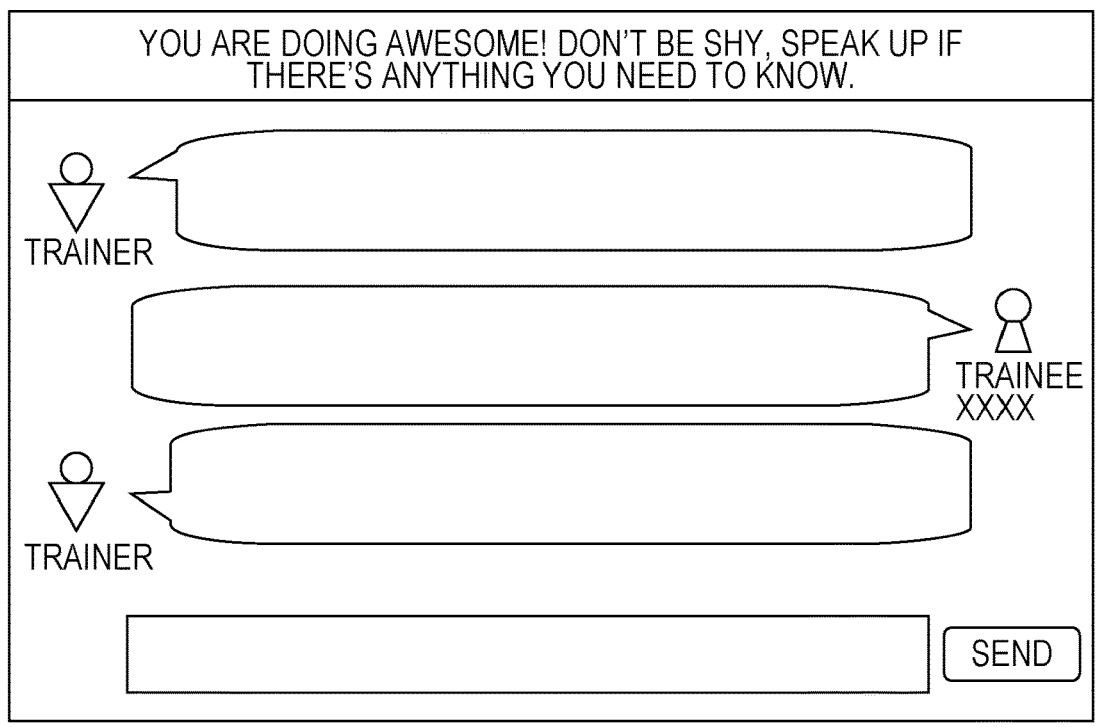
FIG. 11A is a diagram illustrating still another example of the communication screens of the embodiment.
Figure 11B:
FIG. 11B is a diagram illustrating another example of the membership information screen of the embodiment.

In this process, the feedback unit 304 transmits to the trainer's and trainee's display data change units 306 and 307, a feedback string of "You are doing awesome!Don't be shy, speak up if there's anything you need to know." corresponding to the trainee display type "B". As a result, the string of "You are doing awesome!Don't be shy, speak up if there's anything you need to know." is displayed on the communication screens and the membership information screen as illustrated in FIGS. 11A and 11B (S1006).

Herein, the description is back to the step S1001. When the number of completed workouts is equal to or smaller than the target number of workouts (NO in S1001), the determination unit 303 compares the number of messages transmitted from the trainee to the trainer with the threshold of transmitted messages (S1009).

When the number of messages transmitted from the trainee to the trainer is larger than the threshold of transmitted messages (YES in S1009), the determination unit 303 changes the limit status of message transmission to ON (S1010). Specifically, the determination unit 303 updates the value of the limit status field 404 of the membership information 400 of the trainee to ON. In other words, the determination unit 303 prohibits the message transmission from the trainee to the trainer when the number of completed workouts is smaller than the predetermined target number of workouts and the number of messages transmitted from the trainee to the trainer is larger than the predetermined threshold of transmitted messages.

Moreover, the determination unit 303 changes the trainee display type to a display type which indicates that the trainer wants the trainee to transmit a message after executing workout. Specifically, the determination unit 303 sets the trainee display type to "C" and registers the determined trainee display type in the display type field 406 of the membership information 400.

Figure 12:
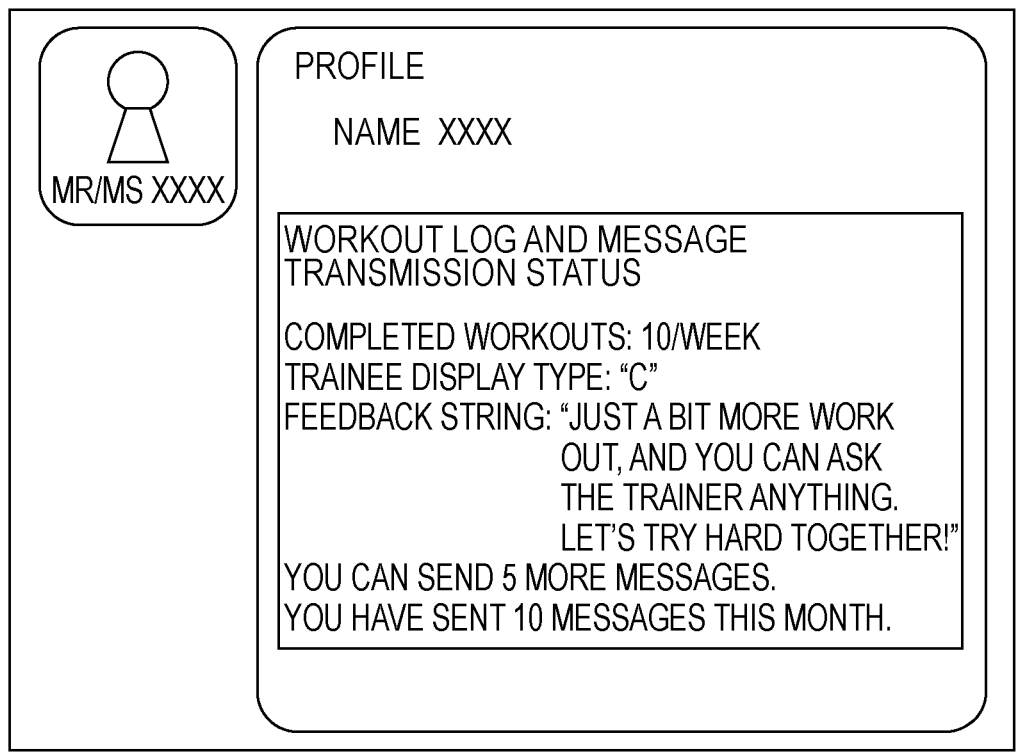
FIG. 12 is a diagram illustrating still another example of the membership information screen of the embodiment.

In this process, the feedback unit 304 transmits to the trainer's and trainee's display data change units 306 and 307, a feedback string of "Just a bit more workout, and you can ask the trainer anything. Let's try hard together!" corresponding to the trainee display type of "C". As a result, the string of "Just a bit more workout, and you can ask the trainer anything. Let's try hard together!" is displayed on the communication screens and the membership information screen as illustrated in FIGS. 7 and 12 (S1011).

Figure 7:
FIG. 7 is a diagram illustrating another example of communication screens of the embodiment.

In the example illustrated in FIG. 7, the trainee feedback string is displayed over the entire screen, so that the trainee cannot input and transmit a message at this time. In other words, the message transmission from the trainee to the trainer on the communication screen is prohibited.

Note that the feedback string may be displayed in the field 601 of FIG. 6. The feedback string may be displayed when the trainee tries to input a string.

On the other hand, when the number of transmitted messages is equal to or not larger than the threshold of transmitted messages (NO in S1009), the determination unit 303 sets the trainee display type to a display type which indicates that the trainer wants the trainee to work out positively. Specifically, the determination unit 303 sets the trainee display type to "D" and registers the determined trainee display type in the display type field 406 of the membership information 400.

Figure 13A:
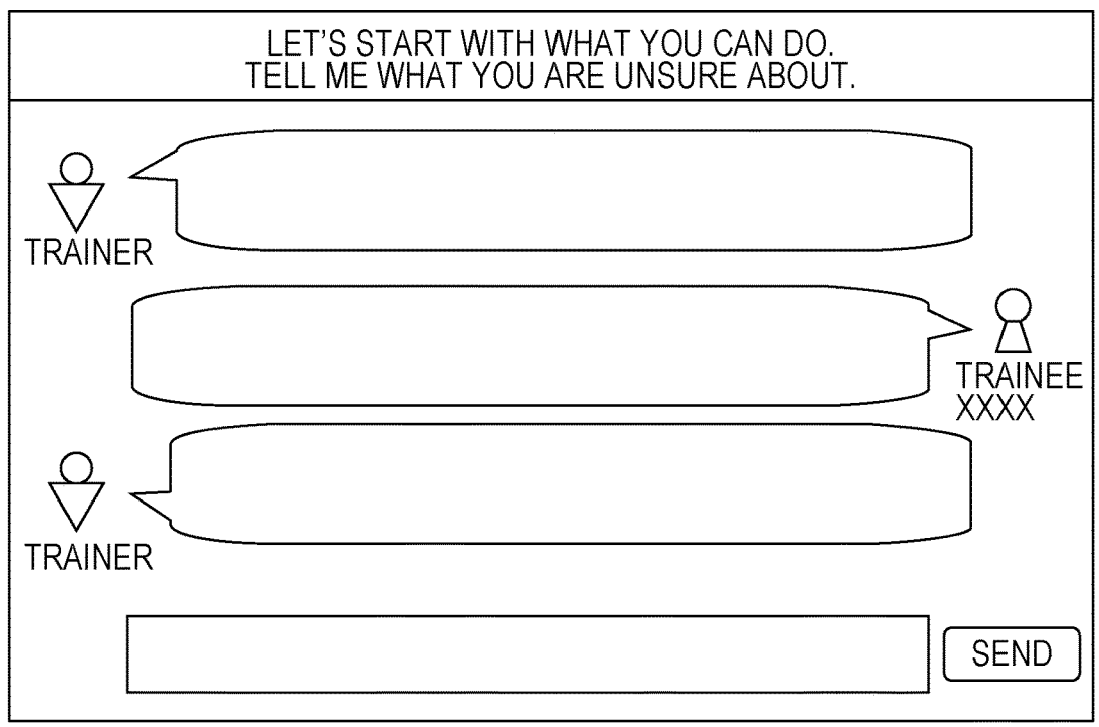
FIG. 13A is a diagram illustrating still another example of the communication screen of the embodiment.
Figure 13B:
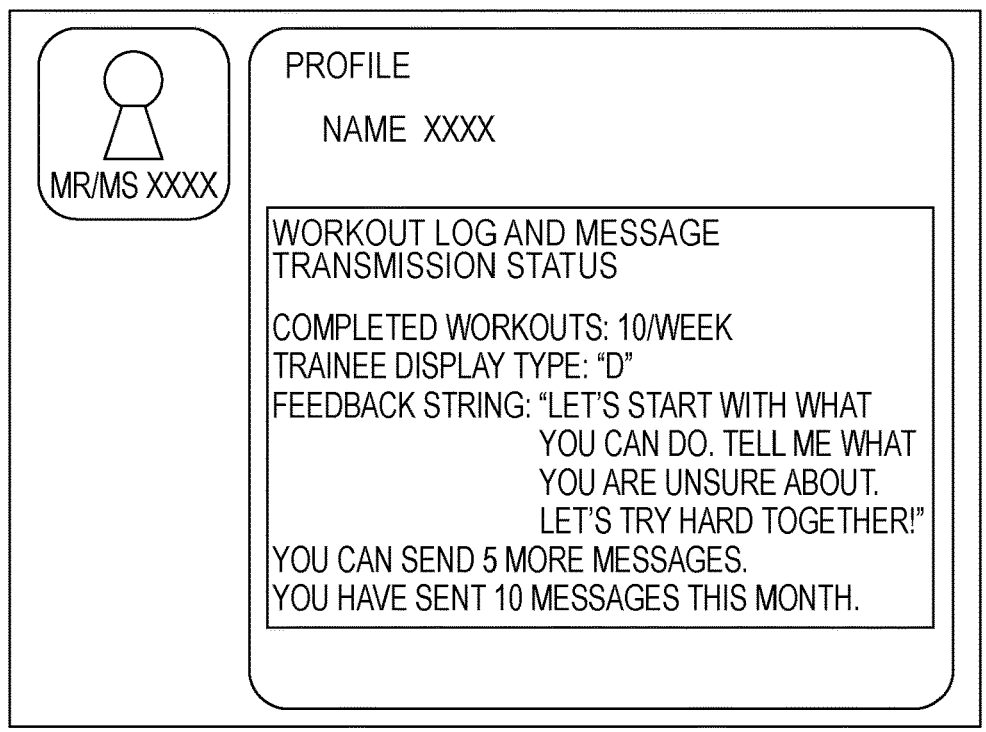
FIG. 13B is a diagram illustrating still another example of the membership information screens of the embodiment.

In this process, the feedback unit 304 transmits to the trainer's and trainee's display data change units 306 and 307, a feedback string of "Let's start with what you can do. Tell me what you are unsure about." corresponding to the trainee display type of "D". As a result, the string of "Let's start with what you can do. Tell me what you are unsure about." is displayed on the communication screens and the membership information screen as illustrated in FIGS. 13A and 13B (S1012).

Effects

With the communication determination unit 206 according to the embodiment, it is possible to control permission and prohibition of the message transmission from the trainee to the trainer on the communication screens based on the workout log data and the transmission status data. Accordingly, it is possible to prohibit transmission of unnecessary messages from the trainee to the trainer. Moreover, by replying to a message received from the trainee who is permitted to transmit messages, the trainer can send advice and answers appropriate for the trainee and can keep up the trainee's motivation.

Moreover, with the communication determination unit 206 according to the embodiment, the message transmission is permitted when the number of workouts completed by the trainee is larger than the predetermined target number of workouts. Accordingly, the online coaching system allows the trainer to increase the trainee's motivation to work out while reducing the burden on the trainer due to online communication with trainees.

Furthermore, with the communication determination unit 206 according to the embodiment, permission and prohibition of the message transmission can be controlled based on the number of workouts completed and the number of messages transmitted. Accordingly, the online coaching system can suppress an increase in the number of messages transmitted, thus reducing the burden on the trainer.

Still furthermore, with the communication determination unit 206 according to the embodiment, the phrase to be displayed on the communication screen is determined based on the number of workouts completed and the number of messages transmitted. Accordingly, the trainer and the trainee check the phrase displayed on the communication screens to know the workout log and the message transmission status and keep up motivation for the workouts and the message transmission.

Still furthermore, with the communication determination unit 206 according to the embodiment, permission and prohibition of the message transmission can be controlled based on the number of uploads of vital data. Accordingly, it is possible to promote uploading of vital data.

Modification of Embodiment

Hereinabove, the online coaching system according to one or plural aspects is described based on the embodiment. However, the present disclosure is not limited to the embodiment. Various modifications of the embodiment that can be conceived by those skilled in the art may be included in the scope of the one or plural aspects without departing from the spirit of the present disclosure.

In the aforementioned embodiment, for example, the communication determination unit 206 is included in the cloud server 1111. However, the communication determination unit 206 may be included in the trainer's device 1002 and trainee's device 1102, or may be implemented as one device (a control device) including the communication determination unit 206.

In the aforementioned embodiment, the plural storage units (the workout log storage unit 201, membership information storage unit 202, and operation history storage unit 207) are included in the cloud server 1111, but the present disclosure is not limited thereto. The plural storage units may be included in a storage device connected to the cloud server 1111 via a network.

In the aforementioned embodiment, the feedback string is displayed on the communication screens. However, images, diagrams, or symbols may be displayed instead of the feedback string.

The online coaching system is applied to the fitness club in the example described in the above embodiment. However, the present disclosure is not limited thereto. The online coaching system may be applied to rehabilitation facilities instructing workouts for recovery from injuries, companies and associations instructing simple anti-aging workouts, or hospitals offering specific health guidance, for example.

The online coaching system according to the embodiment may be used in online communication between a physical therapist and patients assigned to the physical therapist, for example. This allows the physical therapist to carefully support patients who transmit few messages and show little reaction.

Moreover, the online coaching system according to the embodiment is not only applied to fitness clubs and rehabilitation facilities but also applied to sport schools (such as golf, tennis, soccer, and baseball schools). For example, the online coaching system transmits a menu to improve golf swing from a trainer to trainees as students. The trainees work out in accordance with the menu and send question messages to the trainer using the communication screens.

It should be noted that in order to implement more real-time online communication between the trainer and each trainee, the online coaching system may notify the trainer of the trainee's presence (whether the trainee is viewing a video or whether the trainee is operating the device). Specifically, the online coaching system notifies the trainer that the trainee is viewing a workout video. Moreover, the online coaching system estimates the time when the trainee finishes viewing the workout video based on the length of the workout video that the trainee is viewing and notifies the trainer of the estimated time. Accordingly, the trainer can send an advice message to the trainee based on the time when the trainee is estimated to finish viewing the video.

The message from the trainer to the trainee when the trainee finishes viewing a workout video may be transmitted automatically.

It should be noted that the online coaching system may change the order of trainees in the list including plural trainees who receive coaching from the trainer based on the workout log data and the message transmission status data. For example, the online coaching system displays trainees whose limit status is ON in the bottom of the list and displays trainees needing support in upper part. This can clarify trainees who need to communicate with the trainer.

Alternatively, the order of members (trainees) displayed in the list may be changed in accordance with the presence of each trainee (whether the trainee is viewing a workout video or whether the trainee is operating the device). Specifically, the trainee who is viewing a workout video is displayed in upper part of the list, so that the trainer can send a message on the communication screen immediately after the trainee finishes viewing the workout video.

The threshold m of transmitted messages may be freely set for each trainee by the trainer. Moreover, the threshold m of transmitted messages may be set to the same number for all the trainees using the service by the system administrator.

It should be noted that in the aforementioned embodiment, the workout log data represents the number of workouts completed, but the present disclosure is not limited thereto. For example, the workout log data may represent the number of times the trainee's vital data measured by the trainee using a device is uploaded to the cloud server. Moreover, the workout log data may include the number of times the trainee has registered contents of meal to the cloud server, for example. Even in these cases, it is possible to reduce the burden on the trainer if permission and prohibition of the message transmission is controlled based on the result of comparison between the number of times included in the workout log data and the target number of workouts.

It should be noted that in the aforementioned embodiment, the messages displayed on the communication screen are strings inputted by the trainer or the trainee, but the present disclosure is not limited thereto. The communication screen may display the history of operations performed by the trainer or the history of operations performed by the trainee. For example, the online coaching system may display on the communication screen, a message representing that the workout menu for the trainee who receives coaching from the trainer is created. Specifically, the online coaching system may display a message of "You have received a new workout menu." on the communication screen when the trainer creates a workout menu.

Meanwhile, when the trainer cannot reply a message immediately (for example, when the trainer is on vacation or is tied up with another job), the online coaching system may input a message on the communication screen instead of the trainer. Specifically, in the case where the trainer's schedule data indicates that the trainer is on vacation, the online coaching system may input a message of "I'll send you detailed advice tomorrow. See you tomorrow." instead of the trainer when the trainee who receives coaching from the trainer finishes viewing the workout video.

It should be noted that any file may be attached to messages from the trainee to the trainer and messages from the trainer to the trainee. Specifically, each trainee may attach video or a static image of the trainee to a message to be sent to the trainer. This allows the trainee to send video or a static image of workouts of the trainee to the trainer. Accordingly, the trainer can send an advice message to the trainee after viewing the sent video or static image of the trainee.

Moreover, the trainer may send a message to the trainee on the communication screen with video or a static image of the trainer attached thereto.

Furthermore, data may be attached to a message from the trainee to the trainer. Specifically, vital data of the trainee may be attached to a message from the trainee to the trainer.

It should be noted that the technique described in the above aspect can be implemented in the following types of cloud services, for example. However, the types of cloud services where the technique described in the above aspect are implemented are not limited to the following types.

(Service Type 1: In-House Data Center-Type Cloud Service)

Figure 14:
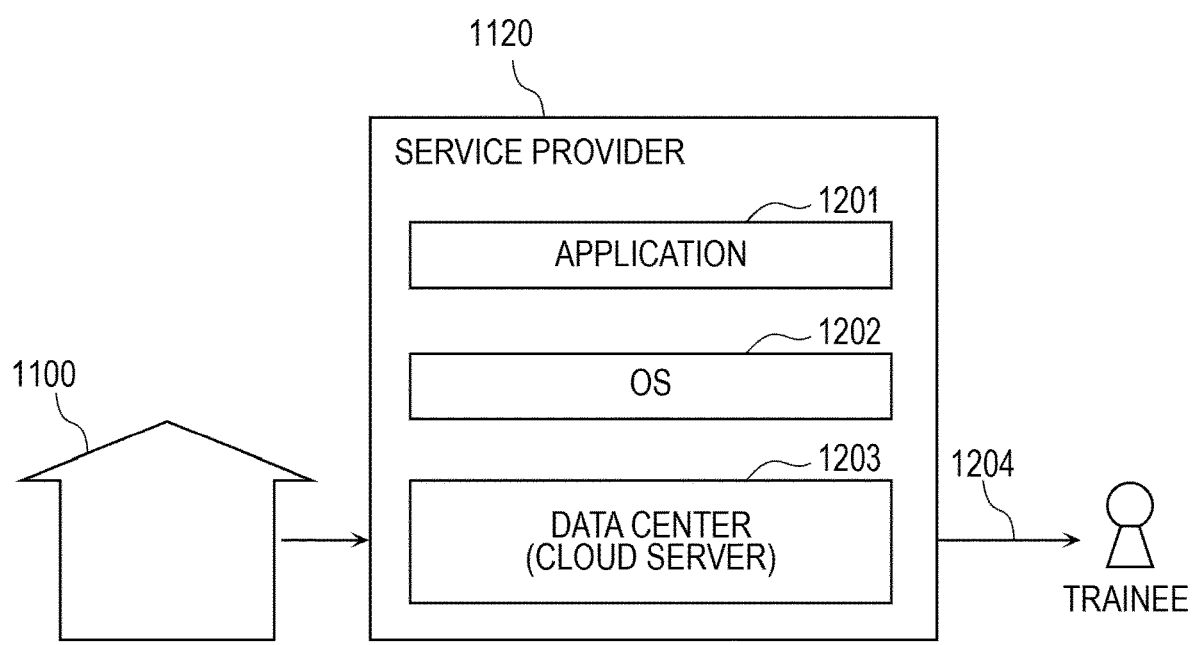
FIG. 14 is a diagram illustrating an entire image of a service provided by the online coaching system in service type 1 (in-house data center-type cloud service)

FIG. 14 is a diagram illustrating the entire image of the service provided by the online coaching system in service type 1 (in-house data center-type cloud service). In the service type 1, a service provider 1120 acquires information from the trainee group 1100 to provide a service to a trainee. In the service type 1, the service provider 1120 has a function as a data center operating company. In other words, the service provider 1120 includes the cloud server 1111 managing big data. Therefore, no data center operating company exists.

In the service type 1, the service provider 1120 operates and manages a data center (cloud server) 1203. Moreover, the service provider 1120 manages an operating system (OS) 1202 and an application 1201. The service provider 1120 provides a service by using the OS 1202 and the application 1201, which are managed by the service provider 1120 (indicated by arrow 1204).

(Service Type 2: IaaS-Type Cloud Service)

Figure 15:
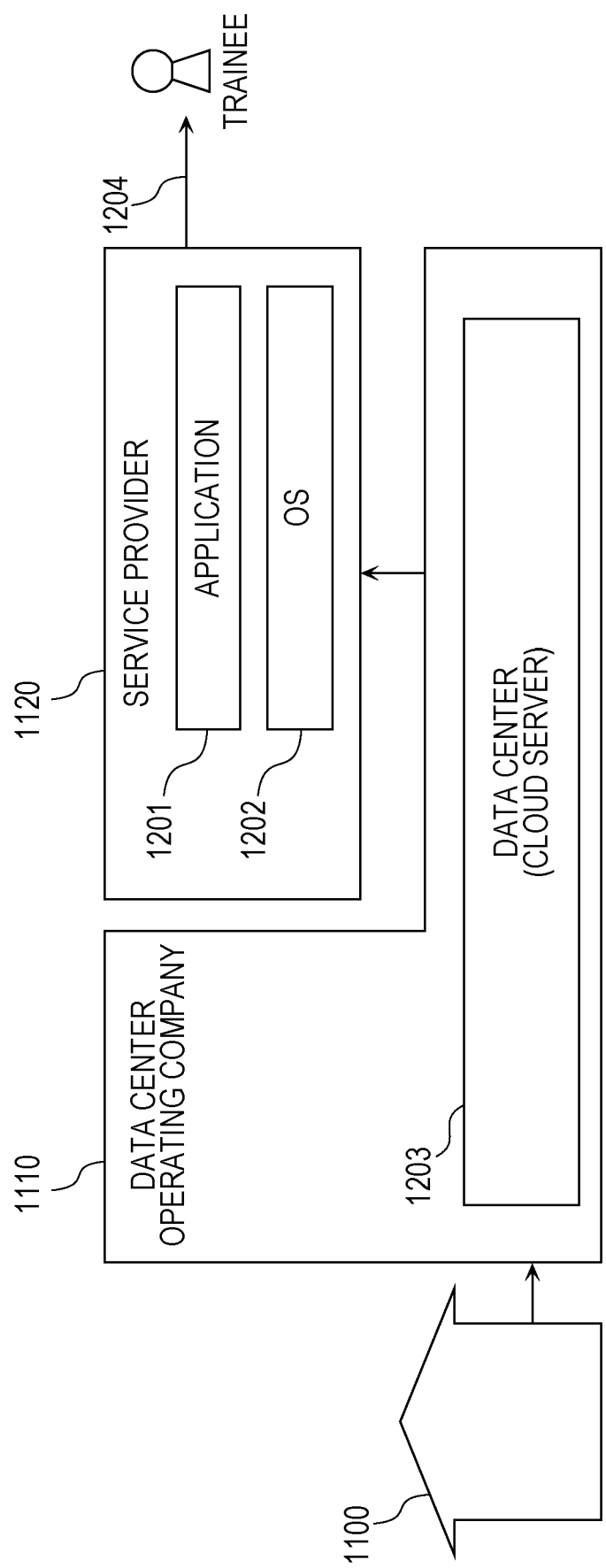
FIG. 15 is a diagram illustrating an entire image of a service provided by the online coaching system in service type 2 (IaaS type cloud service)

FIG. 15 is a diagram illustrating the entire image of the service provided by the online coaching system in service type 2 (IaaS-type cloud service). Herein, IaaS is an abbreviation of Infrastructure as a Service and is a cloud service providing model that provides an infrastructure to build and operate a computer system as a service via the Internet.

In the service type 2, the data center operating company 1110 operates and manages the data center (cloud server) 1203. The service provider 1120 manages the OS 1202 and the application 1201. The service provider 1120 provides a service by using the OS 1202 and the application 1201, which are managed by the service provider 1120 (indicated by arrow 1204).

(Service Type 3: PaaS-Type Cloud Service)

Figure 16:
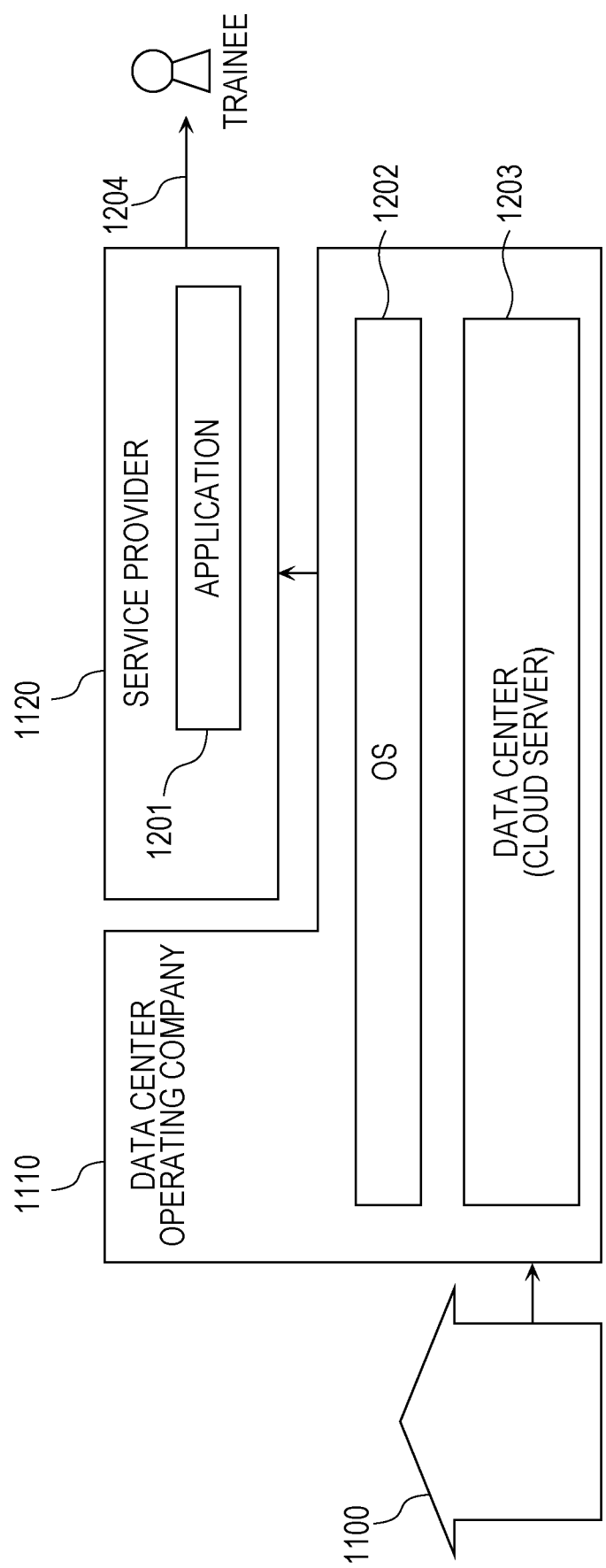
FIG. 16 is a diagram illustrating an entire image of a service provided by the online coaching system of service type 3 (PaaS type cloud service)

FIG. 16 is a diagram illustrating the entire image of the service provided by the online coaching system in service type 3 (PaaS-type cloud service). Herein, PaaS is an abbreviation of Platform as a Service and is a cloud service providing model that provides a platform serving as a base for building and operating software as a service via the Internet.

In the service type 3, the data center operating company 1110 manages the OS 1202 and operates and manages the data center (cloud server) 1203. The service provider 1120 manages the application 1201. The service provider 1120 provides a service by using the OS 1202, which is managed by the data center operating company 1110, and the application 1201, which is managed by the service provider 1120 (indicated by arrow 1204).

(Service Type 4: SaaS-Type Cloud Service)

Figure 17:
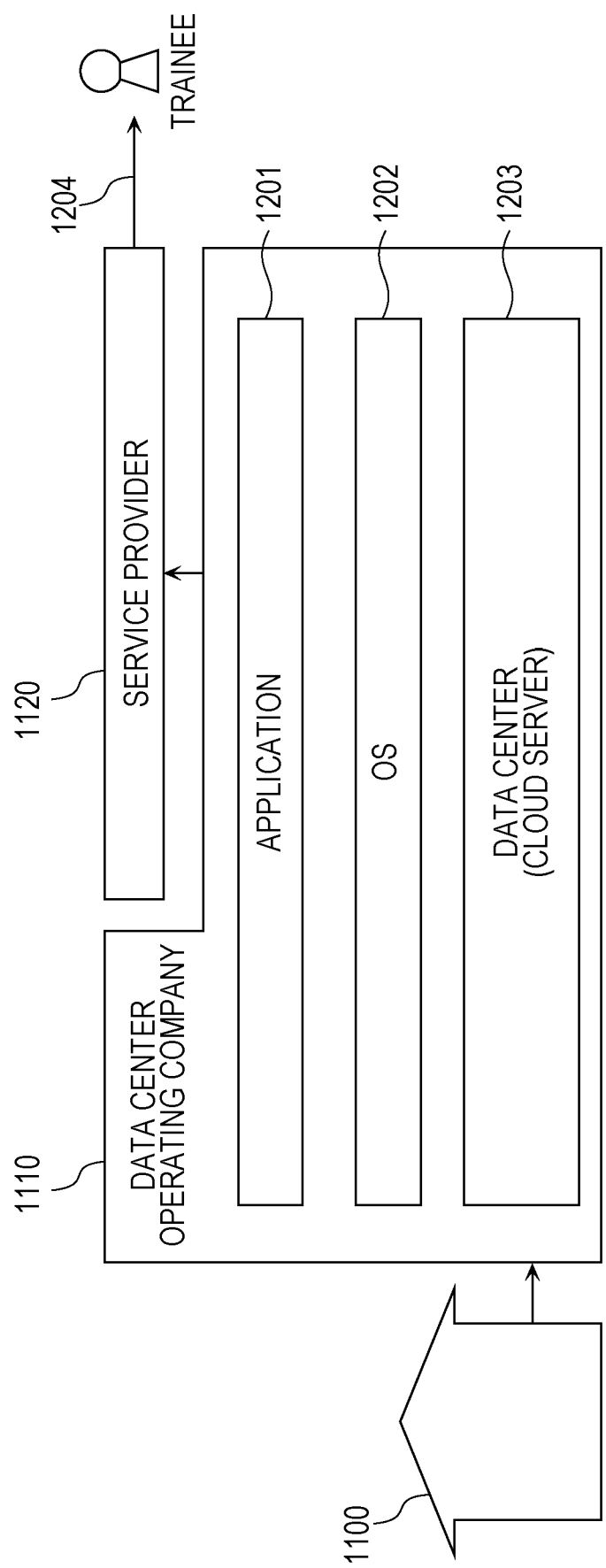
FIG. 17 is a diagram illustrating an entire image of a service provided by the online coaching system in service type 4 (SaaS type cloud service).

FIG. 17 is a diagram illustrating the entire image of the service provided by the online coaching system in service type 4 (SaaS-type cloud service). Herein, SaaS is an abbreviation of Software as a Service. The SaaS-type cloud service is a cloud service providing model having a function of allowing users (including companies and individuals) not having a data center (cloud server) to use applications provided by a platform provider having a data center (cloud server) via a network such as the Internet, for example.

In the service type 4, the data center operating company 1110 manages the application 1201, manages the OS 1202, and operates and manages the data center (cloud server) 1203. The service provider 1120 provides a service by using the OS 1202 and the application 1201, which are managed by the data center operating company 1110 (indicated by arrow 1204).

In any type of the aforementioned cloud services, the service provider 1120 provides a service. Moreover, for example, the service provider or the data center operating company may develop the OS, applications, databases of big data, and the like by itself or outsource development thereof to a third party.

The online coaching system and the online coaching method in the present disclosure are useful as an online coaching system and an online coaching method which enable online communication between trainers and trainees.

What is claimed is:

1. An online coaching method, comprising:
   acquiring, via a network interface, workout log data representing progress of a workout carried out by a trainee, the trainee receiving coaching for the workout from a trainer, the workout log data being measured by a first device;
   determining, with a processor, a status of a message transmission from a second device of the trainee to a third device of the trainer based on acquisition of the workout log data;
   determining, with the processor, a phrase to be displayed on a communication screen of the second device of the trainee based on a result of a comparison between a number of workouts completed by the trainee and a predetermined target number of workouts and a result of a comparison between a number of messages transmitted and a predetermined threshold of transmitted messages; and controlling permission and prohibition of the message transmission from the second device of the trainee to the third device of the trainer based on the status of the message transmission, the message transmission including a question from the trainee to the trainer, wherein the message transmission from the second device of the trainee to the third device of the trainer is permitted in a case where a predetermined target condition corresponding to the workout carried out by the trainee is satisfied, the message transmission from the second device of the trainee to the third device of the trainer is prohibited in a case where the predetermined target condition corresponding to the workout carried out by the trainee is not satisfied, the message transmission from the second device of the trainee to the third device of the trainer being prohibited by displaying the phrase over an entire screen of the second device of the trainee so that a message cannot be input and transmitted by the trainee, the workout log data, which is measured by the first device, includes vital data of the trainee, the first device being capable of measuring the vital data, and the first device, which measures the workout log data including the vital data of the trainee, includes at least one of an activity tracker or a heart rate meter.

2. The online coaching method according to claim 1, wherein the workout log data further includes the number of workouts completed by the trainee, and the message transmission from the second device of the trainee to the third device of the trainer is permitted in a case where the number of workouts completed by the trainee is larger than a predetermined target number of workouts.

3. The online coaching method according to claim 2, further comprising: determining, with the processor, the number of messages transmitted from the trainee to the trainer for a predetermined period of time, and the message transmission from the second device of the trainee to the third device of the trainer is prohibited in a case where the number of workouts completed by the trainee is not larger than the predetermined target number of workouts and the number of messages transmitted from the trainee to the trainer is larger than the predetermined threshold of transmitted messages.

4. The online coaching method according to claim 1, wherein
the workout log data further includes a number of uploads of the measured vital data to a server, and
the message transmission from the second device of the trainee to the third device of the trainer is permitted in a case where the number of uploads of the measured vital data is larger than a predetermined target number of uploads.

5. The online coaching method according to claim 1, wherein the predetermined target condition corresponding to the workout carried out by the trainee is configured to be increased by the trainer for increasing a motivation of the trainee for the workout.

6. The online coaching method according to claim 1, wherein the permission and the prohibition of the message transmission from the second device of the trainee to the third device of the trainer is controlled based on the status of the message transmission, which is determined based on the acquisition of the workout log data, to promote uploading of the vital data, which the workout log data includes.

7. The online coaching method according to claim 1, wherein the permission and the prohibition of the message transmission from the second device of the trainee to the third device of the trainer is controlled based on the status of the message transmission for reducing a burden on the trainer.

8. An online coaching system, comprising:
a first device which measures workout log data representing progress of a workout carried out by a trainee, the trainee receiving coaching for the workout from a trainer;
a second device which is used by the trainee;
a third device which is used by the trainer; and
a server connected to the first device, the second device, and the third device, wherein the server includes one or more memories and circuitry which, in operation, performs operations including:
acquiring the workout log data;
determining a status of a message transmission from the second device of the trainee to the third device of the trainer;
determining a phrase to be displayed on a communication screen of the second device of the trainee based on a result of a comparison between a number of workouts completed by the trainee and a predetermined target number of workouts and a result of a comparison between a number of messages transmitted and a predetermined threshold of transmitted messages; and
controlling permission and prohibition of the message transmission from the second device of the trainee to the third device of the trainer based on the status of the message transmission, the message transmission including a question from the trainee to the trainer,
the message transmission from the second device of the trainee to the third device of the trainer is permitted in a case where a predetermined target condition corresponding to the workout carried out by the trainee is satisfied,
the message transmission from the second device of the trainee to the third device of the trainer is prohibited in a case where the predetermined target condition corresponding to the workout carried out by the trainee is not satisfied, the message transmission from the second device of the trainee to the third device of the trainer being prohibited by displaying the phrase over an entire screen of the second device of the trainee so that a message cannot be input and transmitted by the trainee,
the workout log data, which is measured by the first device, includes vital data of the trainee, the first device being capable of measuring the vital data, and
the first device, which measures the workout log data including the vital data of the trainee, includes at least one of an activity tracker or a heart rate meter.

9. The online coaching system according to claim 8, wherein the predetermined target condition corresponding to the workout carried out by the trainee is configured to be increased by the trainer for increasing a motivation of the trainee for the workout.

10. The online coaching system according to claim 8, wherein the permission and the prohibition of the message transmission from the second device of the trainee to the third device of the trainer is controlled based on the status of the message transmission, which is determined based on the acquisition of the workout log data, to promote uploading of the vital data, which the workout log data includes.

11. The online coaching system according to claim 8, wherein the permission and the prohibition of the message transmission from the second device of the trainee to the third device of the trainer is controlled based on the status of the message transmission for reducing a burden on the trainer.

12. A control device, comprising:
one or more memories; and
circuitry which, in operation, performs operations including:
acquiring workout log data representing progress of a workout carried out by a trainee, the trainee receiving coaching for the workout from a trainer, the workout log data being measured by a first device;
determining a status of a message transmission from a second device of the trainee to a third device of the trainer based on acquisition of the workout log data;
determining a phrase to be displayed on a communication screen of the second device of the trainee based on a result of a comparison between a number of workouts completed by the trainee and a predetermined target number of workouts and a result of a comparison between a number of messages transmitted and a predetermined threshold of transmitted messages; and
controlling permission and prohibition of the message transmission from the second device of the trainee to the third device of the trainer based on the status of the message transmission, the message transmission including a question from the trainee to the trainer,
wherein the message transmission from the second device of the trainee to the third device of the trainer is permitted in a case where a predetermined target condition corresponding to the workout carried out by the trainee is satisfied,
the message transmission from the second device of the trainee to the third device of the trainer is prohibited in a case where the predetermined target condition corresponding to the workout carried out by the trainee is not satisfied, the message transmission from the second device of the trainee to the third device of the trainer being prohibited by displaying the phrase over an entire screen of the second device of the trainee so that a message cannot be input and transmitted by the trainee,
the workout log data, which is measured by the first device, includes vital data of the trainee, the first device being capable of measuring the vital data, and
the first device, which measures the workout log data including the vital data of the trainee, includes at least one of an activity tracker or a heart rate meter.

13. The control device according to claim 12, wherein the predetermined target condition corresponding to the workout carried out by the trainee is configured to be increased by the trainer for increasing a motivation of the trainee for the workout.

14. The control device according to claim 12, wherein the permission and the prohibition of the message transmission from the second device of the trainee to the third device of the trainer is controlled based on the status of the message transmission, which is determined based on the acquisition of the workout log data, to promote uploading of the vital data, which the workout log data includes.

15. The control device according to claim 12, wherein the permission and the prohibition of the message transmission from the second device of the trainee to the third device of the trainer is controlled based on the status of the message transmission for reducing a burden on the trainer.

\* \* \* \* \*